(12) United States Patent
Harter et al.

(10) Patent No.: US 10,069,918 B2
(45) Date of Patent: Sep. 4, 2018

(54) GLOBAL COMMUNICATION AND CONTROL

(71) Applicant: UT Battelle, LLC, Oak Ridge, TN (US)

(72) Inventors: Andrew Harter, Oak Ridge, TN (US); Brad Stinson, Oak Ridge, TN (US); Erik Kabela, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 307 days.

(21) Appl. No.: 14/938,582

(22) Filed: Nov. 11, 2015

(65) Prior Publication Data
US 2017/0134497 A1    May 11, 2017

(51) Int. Cl.
*G08C 19/22* (2006.01)
*H04L 29/08* (2006.01)
*G01N 33/00* (2006.01)

(52) U.S. Cl.
CPC ......... *H04L 67/12* (2013.01); *G01N 33/0004* (2013.01)

(58) Field of Classification Search
CPC ....................................................... H04L 67/12
See application file for complete search history.

(56) References Cited

U.S. PATENT DOCUMENTS

| | | | |
|---|---|---|---|
| 6,505,165 B1 | 1/2003 | Berstis et al. | |
| 6,930,596 B2 | 8/2005 | Kulesz et al. | |
| 7,049,952 B2 | 5/2006 | Kulesz et al. | |
| 7,218,227 B2 | 5/2007 | Davis et al. | |
| 7,228,210 B2 | 6/2007 | Davis et al. | |
| 7,834,754 B2 | 11/2010 | Kulesz et al. | |
| 8,228,911 B2 | 7/2012 | Cheriyath et al. | |
| 2006/0187017 A1* | 8/2006 | Kulesz ................... | G08B 21/12 340/506 |
| 2008/0147257 A1 | 6/2008 | Kuhlgatz et al. | |
| 2008/0195355 A1* | 8/2008 | Brandt ..................... | G01N 1/26 702/188 |
| 2009/0003216 A1* | 1/2009 | Radunovic ............ | H04L 45/123 370/237 |

(Continued)

FOREIGN PATENT DOCUMENTS

WO    WO 2010/005392 A1    1/2010

OTHER PUBLICATIONS

Lawrence C. Freudinger, "Cyberinfrastructure for Airborne Sensor Webs," NASA Dryden Flight Research Center, Edward California 93536, USA—Lawrence.c.freudinger@nasa.gov, 6 pages.

*Primary Examiner* — Amine Benlagsir
(74) *Attorney, Agent, or Firm* — Brinks Gilson & Lione

(57) ABSTRACT

A process detects media dispersion. The process detects the dispersion of contaminants through distributed remote sensor platforms that connect one or more sensors on a remote device. The process transmits detection data from the distributed remote sensor platform to a radiation tolerant satellite router. A gateway connects the radiation tolerant satellite router to a hardware server and converts the detection data to a compatible form with a protocol used by a hardware server. The process generates a plume model in response to the detection data and meteorological data that models dispersion plumes and activates and deactivates selected sensors in response to a forecasted to dispersion area.

16 Claims, 15 Drawing Sheets
(10 of 15 Drawing Sheet(s) Filed in Color)

(56) References Cited

U.S. PATENT DOCUMENTS

| | | | | |
|---|---|---|---|---|
| 2009/0076665 A1* | 3/2009 | Hoisington | .......... | G05D 1/0044 |
| | | | | 701/2 |
| 2009/0282309 A1* | 11/2009 | Yue | ....................... | H04L 1/1887 |
| | | | | 714/748 |
| 2012/0197600 A1* | 8/2012 | Bai | .................... | G08B 13/1968 |
| | | | | 703/1 |
| 2014/0316616 A1* | 10/2014 | Kugelmass | ............ | G05D 1/101 |
| | | | | 701/8 |
| 2015/0264534 A1* | 9/2015 | Liu | ........................ | H04W 4/04 |
| | | | | 455/456.1 |

* cited by examiner

GLOBAL COMMUNICATION AND CONTROL

STATEMENT REGARDING FEDERALLY SPONSORED RESEARCH AND DEVELOPMENT

This invention was made with United States government support under Contract No. DE-AC05-000R22725 awarded by the United States Department of Energy. The United States government has certain rights in the invention.

BACKGROUND

Technical Field

This disclosure relates to remote monitoring and more specifically to systems/processes that acquire sensor data on a global scale and forecast dispersions.

Related Art

Environmental monitoring can protect the public and the environment from contaminants and pathogens that are released into a variety of media including air, soil, and water. Some pollutants are by-products of vehicle emissions, power plants, refineries, industrial and laboratory processes or intentionally released to harm the public and the environment. Soil and water contaminants may be microbiological (e.g., coliform), radioactive (e.g., tritium), inorganic (e.g., arsenic), synthetic organic (e.g., pesticides), and volatile organic compounds (e.g., benzene). Some contaminants can persist for many years and migrate through large regions of soil until they reach water resources, where they may present an ecological or a health threat.

There are regulations on the concentrations of many environmental contaminants in air and water. However, current monitoring methods are costly, time-intensive, geographically restricted, and limited by sampling and analytical techniques. Currently, the ability to deploy and use sensors in global networks is uncertain due to global and technological barriers. A need exists for accurate inexpensive long-term global monitoring platform that can monitor contaminants using sensors that may be configured, operated, and harvested on site or in position.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

This disclosure describes a remote monitoring architecture that may acquire sensor data on a global scale. The system and process (herein referred to as the system) is fully or partially autonomous. The sampling services it renders enable global sensor, remote data collection, and remote satellite control through wireless communication. The system improves wireless bandwidth throughput by an order of magnitude that further supports encryption and authentication without adding base stations or spectrum. It provides global coverage across oceans, continents, airways, and the polar regions of the earth.

Figure 1:
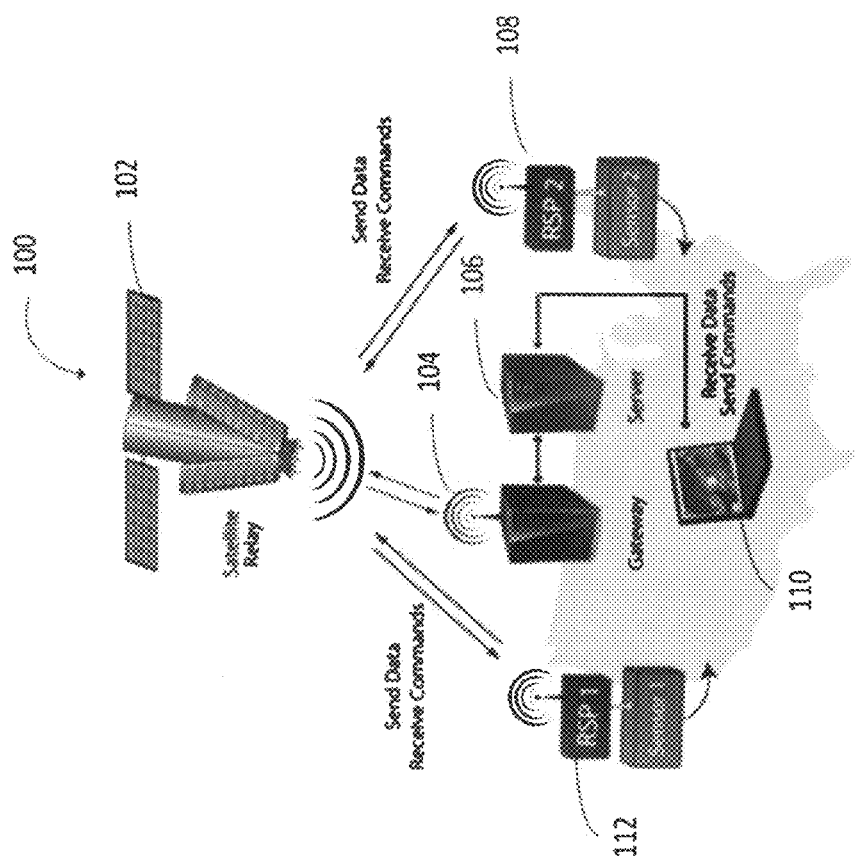
FIG. 1 is a global plug-and-play automated configurable sensor control and data acquisition platform.

FIG. 1 illustrates a global plug-and-play automated configurable sensor control and data acquisition platform. The system 100 expedites message delivery through a hardware radiation tolerant IP router (satellite router) 102 that orbits the earth. The satellite router 102 receives transmitted messages from remote sensor (hardware) platforms (RSP) and wirelessly transmits them to a hardware gateway 104. The gateway 104 interconnects wireless and tangible networks such as a local area network to the satellite router 102. The gateway 104 executes protocol conversions between the satellite router 102 and the wireless/tangible networks, data translations, data conversions, and performs message handling. A hardware information repository and intelligent server 106 tracks and traces communication with one or more RSPs and hardware clients 110. The information repository and intelligent server 106 captures, stores, and analyzes event data at the unit or lot level as data is collected from a local or a remote global area. Once captured the data is processed to detect contaminants, model plumes, and enable and configure additional RSPs and/or sensors that can track and forecast the flow of materials such as gases and aerosols that comprise the plumes. As the plume spreads, the system 100 activates sensors in the projected contaminants paths, harvests data from RSPs and meteorological stations in or near its projected path, and adjusts the plume model to help identify the gases and aerosols (and/or other media) and the paths that it is predicted to follow. The system's smart RSPs and operations can match the real time characteristics of the event allowing the system to respond to a dispersion as it occurs (e.g., at the same rate data is received or at least as fast as that rate or substantially at that rate), positioning, enabling, or generating virtual sensors on RSP's in its projected path, disabling RSP's no longer in its path, while making corrections such as modeling corrections based on measurements, analytics, and forecasts. When errors occur the information repository and intelligent server 106 may automatically execute diagnostic software that may include a diagnostics program that performs network diagnostics and continuity evaluations of the communication links and operations of remote RSPs. When errors are detected the system 100 logs the error and reports the error condition electronically such as through messaging or electronic mail and attempts to mediate the error by executing software diagnostic routines, executing software resets, executing hardware resets, power cycling, and/or etc.

Figure 11:
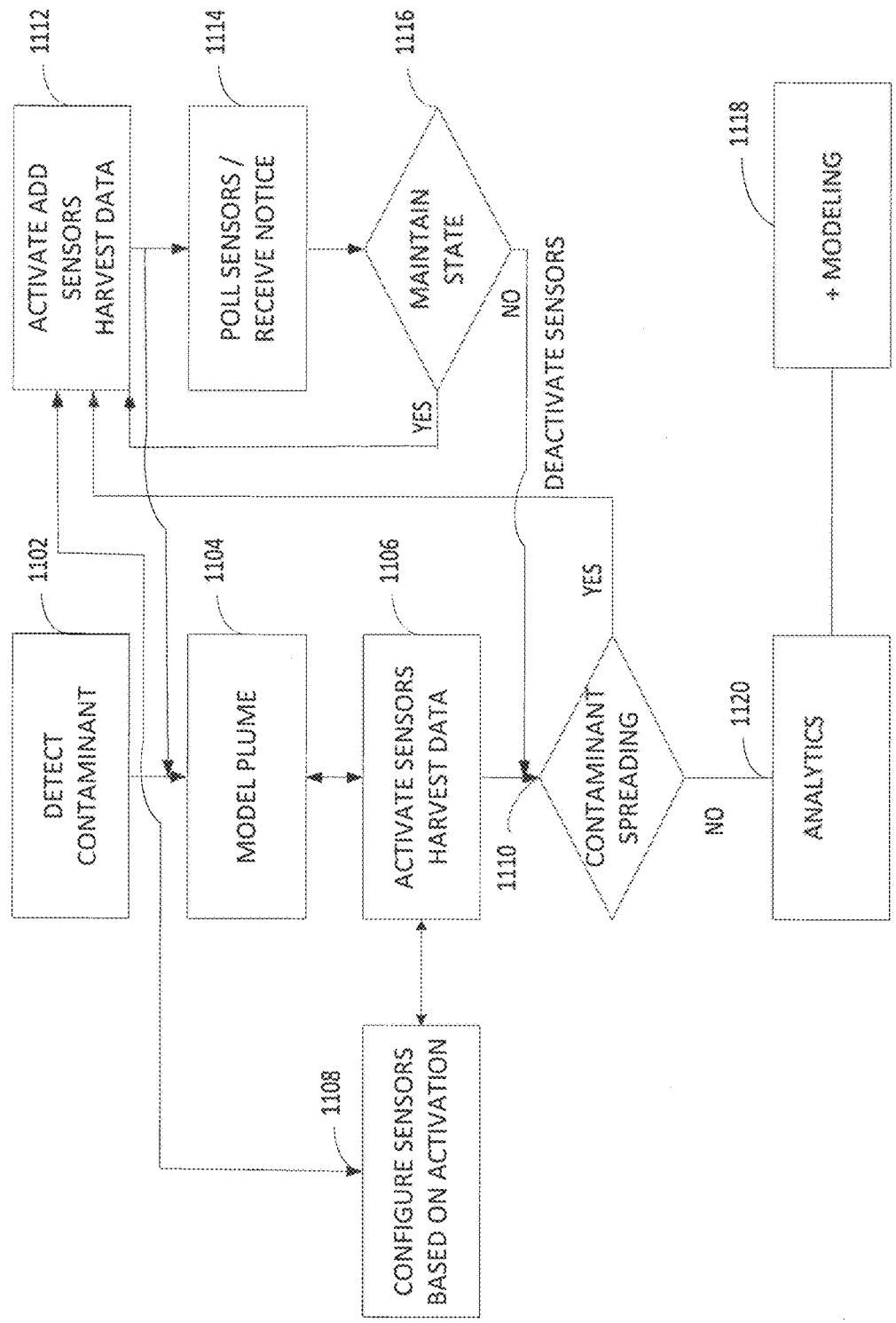
FIG. 11 is exemplary remote monitoring process.
Figure 12:
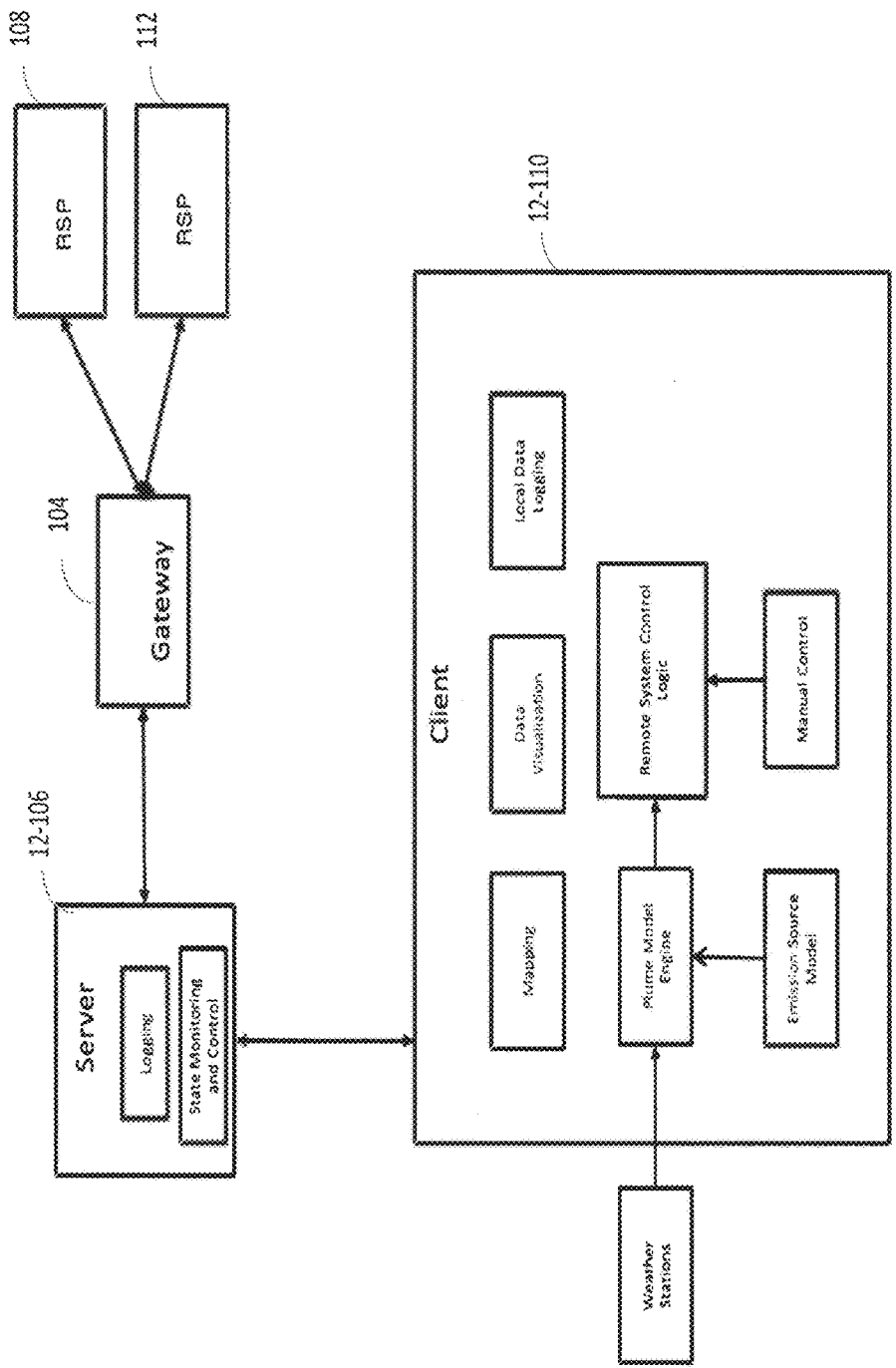
FIG. 12 is an alternate global plug-and-play automated configurable sensor control and data acquisition platform.

The RSPs 108 and 112 shown in FIG. 1 (two are shown, but one or more are used in other systems) are the interfaces to the satellite router 102 and the sensors. The RSPs are the point of interaction or communication between the sensors and electronics that support them and the satellite router 102. The sensors detect and/or measure media, such as a state or characteristic of a gas, aerosol, or air sample, for example, by converting the monitored or detected characteristics of the media into data. Samples are taken at periodic intervals to measure and record a parameter before being converted into analog signals that are then converted into a digital signal. In some systems, the RSPs are embedded within the sensors, which may be embedded in unmanned aerial vehicles (UAVs), meaning they are integrated within or a unitary part of the sensors themselves and/or are integrated within or a unitary part of the UAVs. Some RSPs are autonomously configured in response to the media properties it detects, records, or others responds to and some RSPs are configured in response to client 110 requests or commands. The autonomous and user actuated commands dynamically configure and control the sensors establishing when the RSPs operate or sleep, reset, what properties or characteristics the RSPs detect, what analysis or analytics are performed, what data is sampled, what data is converted into digital data and stored in a local memory and/or transmitted to the satellite router 102. Some RSPs may generate virtual sensors as later described in FIG. 11. Each RSP shown in FIG. 1 may transmit data in response to multiple events: in response to a client request; when a user-defined threshold is exceeded, at a preset or variable duty cycle, when polled, or autonomously in real time as events occur. In this disclosure real time relates to computer systems that process information at least as fast as the same rate the data is received enabling the systems to direct and control the process such as automatically modeling and enabling sensors based on the dispersion models. Some RSPs transmit auto-locate data identifying their geographical areas and their operating states, and automatically establish communication connections with the information repository and intelligent server 106 through short data bursts when enabled.

Figure 2:
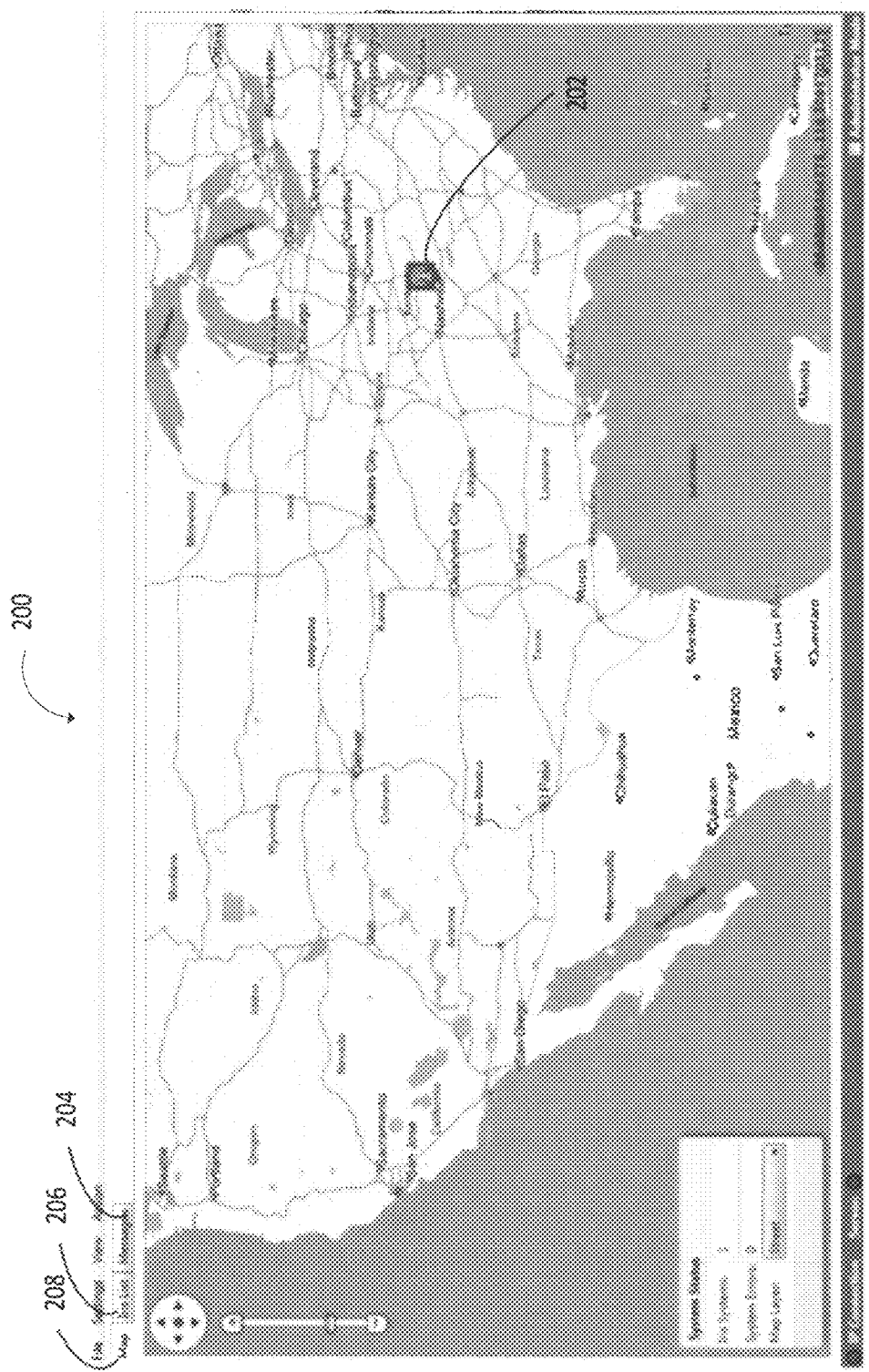
FIG. 2 is a graphic representation of an exemplary remote sensor platform (RSP) shown in its geographical location.
Figure 3:
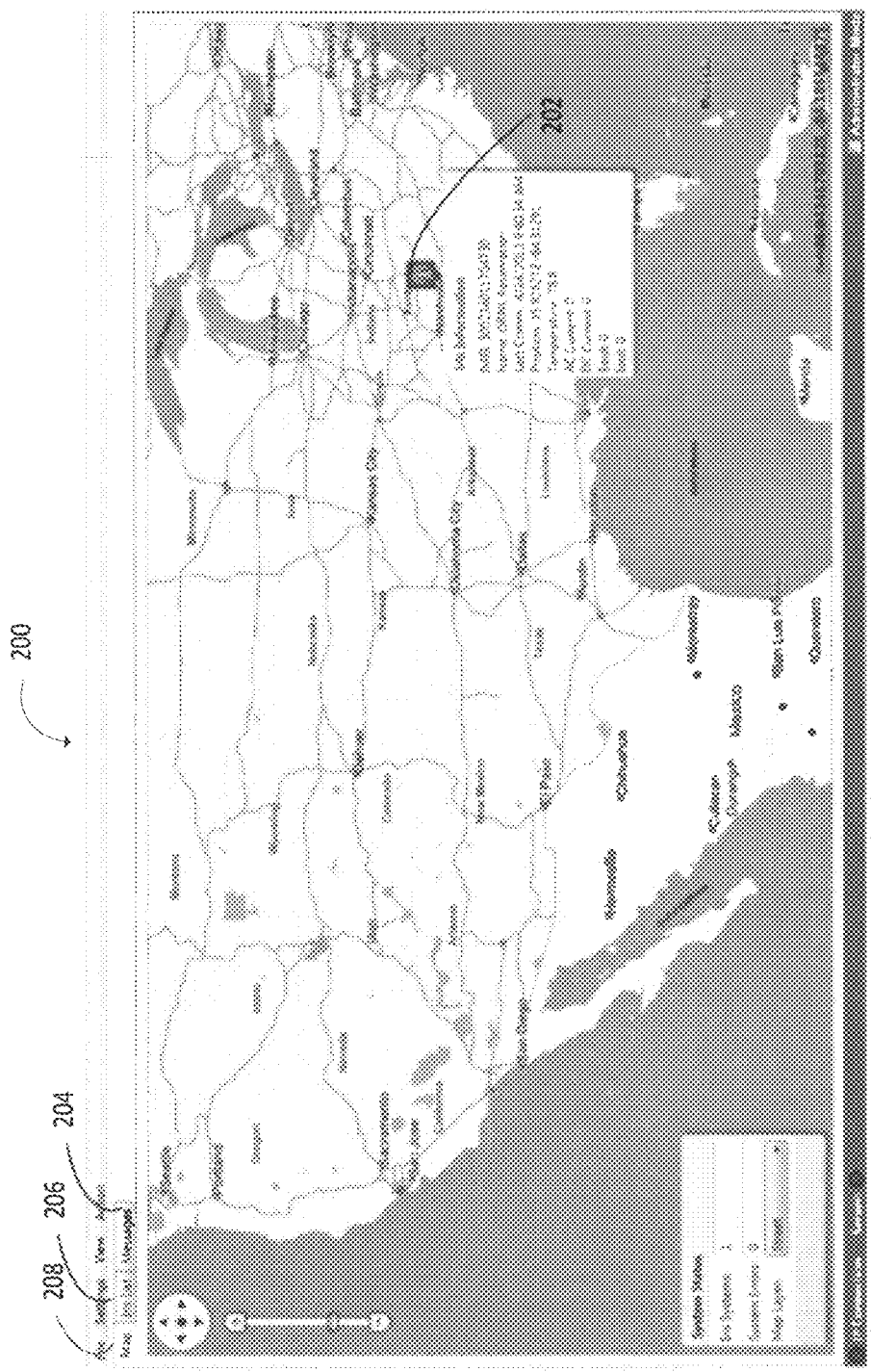
FIG. 3 is a graphic representation of the RSP of FIG. 2 and an exemplary log.
Figure 4:
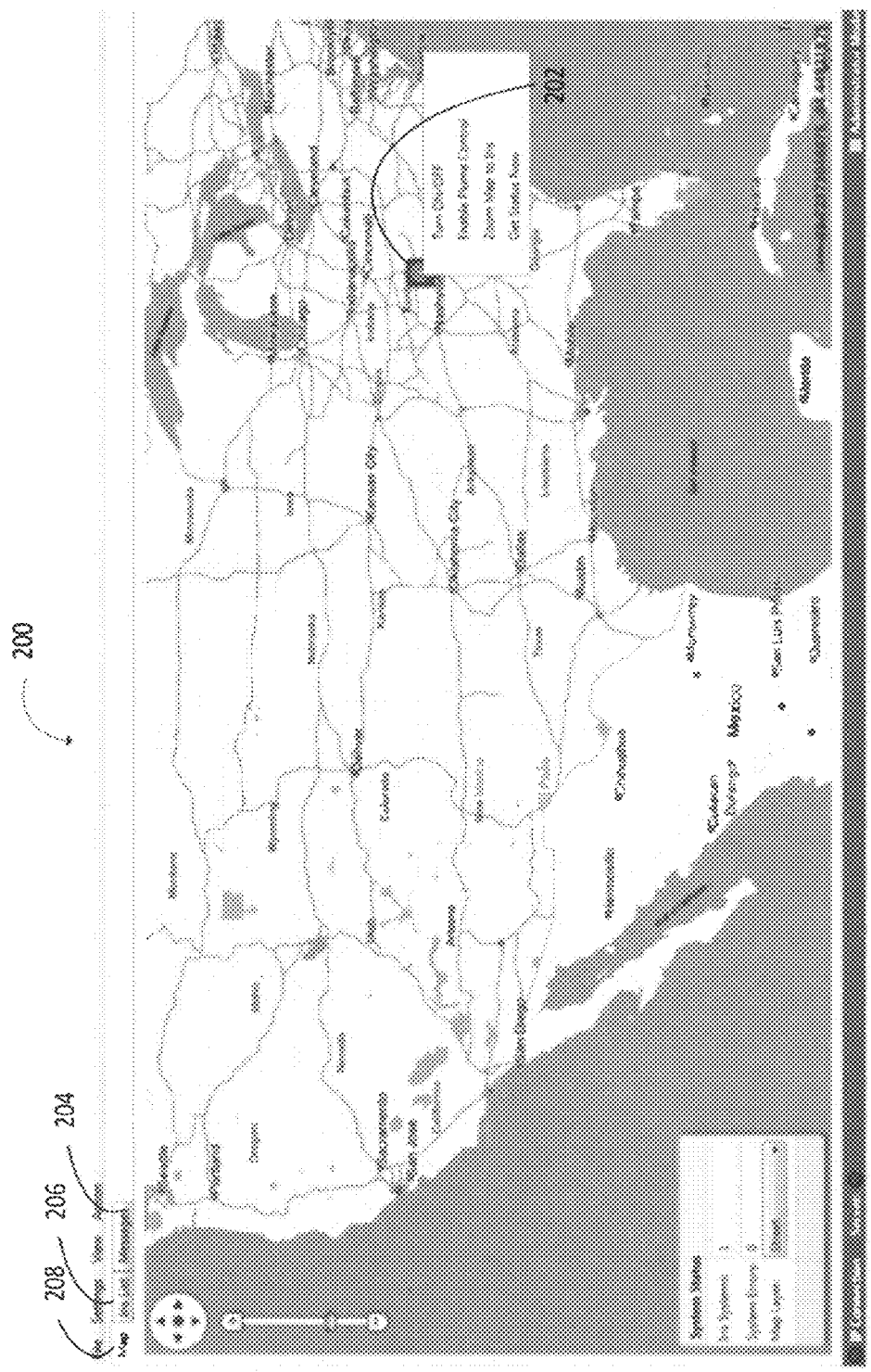
FIG. 4 is a graphic representation of the RSP of FIG. 2 and exemplary software enabled controls.
Figure 5:
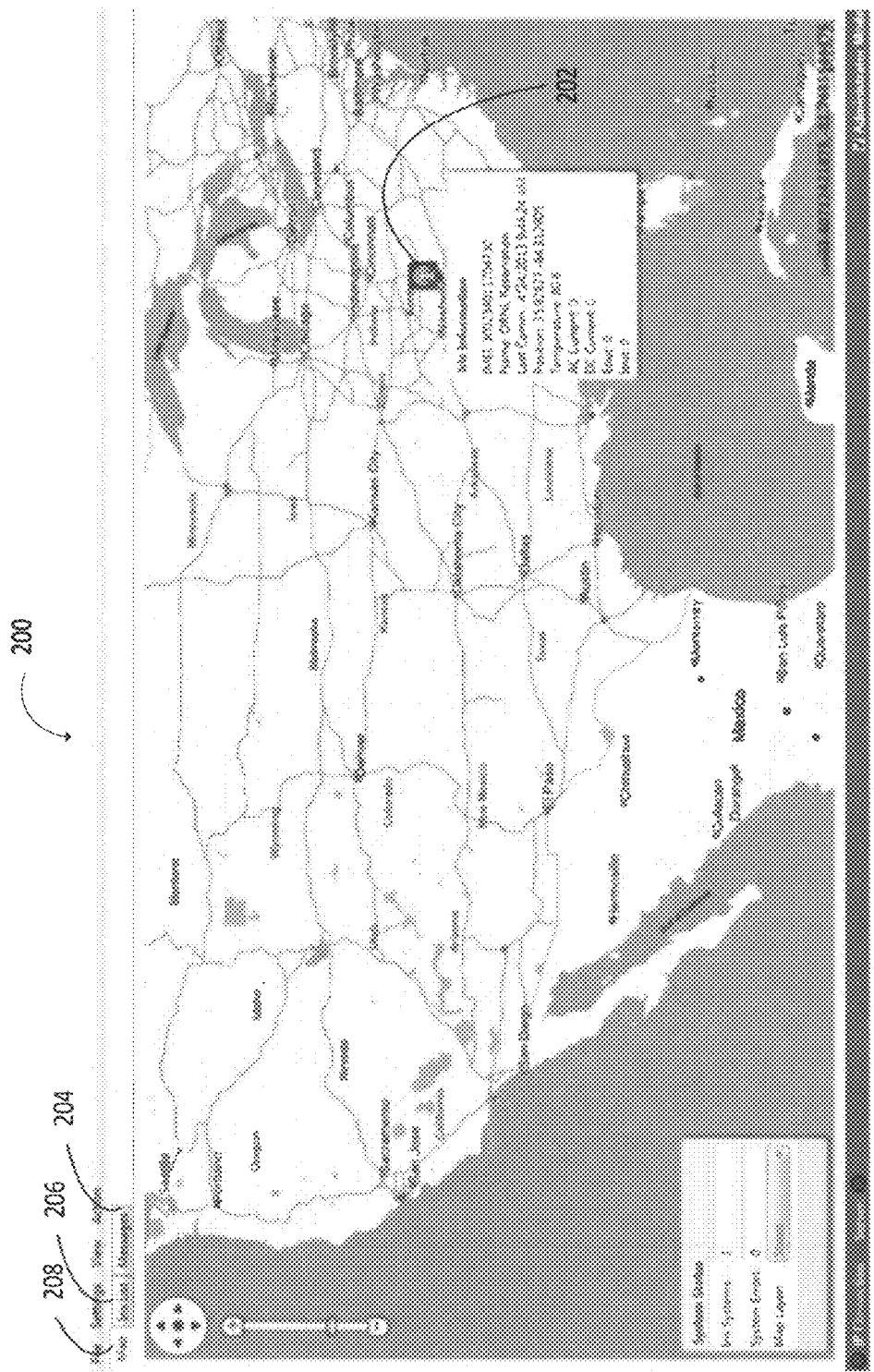
FIG. 5 is a graphic representation of the RSP of FIG. 2 and an exemplary log.

FIG. 2 shows a client-side image map generated by information repository and intelligent server 106. Regions of the image rendered on the display may be selected by hovering over a portion of the display, touching the display, or selecting an input through a hand-activated input device. In FIG. 2 the image mapping generated by server 106 shows the location and state of RSP 202 (rendered via the map tab 208). While one sensor is shown, the map connects multiple RSP across all deployed platforms including fixed platforms, buoyed platforms, mobile platforms: in flight, on the road, etc.). RSP 202's color (red) indicates that the sensor is in an inactive state or in a power saving mode such as a hibernation mode. In hibernation mode, the content of the RSP's volatile memory are copied to a local non-volatile storage before the RSP enters a sleep mode. A complete list of the sensors that are part of the system 100 may be accessed through the "Iris List" tab 206 shown in FIGS. 2-5. And, metadata for the sensor rendered on the screen may be accessed through a database that can be invoked when the user selects a message tab 204. An exemplary record of the database may identify: the station or platform it belongs to, sensor ID, its "latitude (degree)", its "longitude (degree)", its name, its source, its "platform type", its "start date", and/or its "end date."

When a user hovers over the client-side image map the information repository and intelligent server 106 renders a statistical summary of RSP 202. The summary data shown in FIG. 3 includes identifying information; the sensors name, its latitude (degree), its longitude (degree), weather conditions (e.g., temperature), communication status, and operating status, for example. When the region of the image displaying RSP 202 is selected the information repository and intelligent server 106 provides access to other resources linked to the RSP 202 and/or client-side image map. Those resources include actuating a software script or hyperlink that allows the user to control the RSP 202 or enable autonomous control (via a plume control model, for example), allow a user to enlarge a selected portion of the client-side image map (e.g., provide panoramic views of its location details like a street view), and/or directly query the RSP 202. When the RSP 202 is actuated, its visual indicator changes, such as the representation shown in FIG. 5 where RSP is visualized in green to indicate that RSP 202 is in an active operating state.

Figure 6:
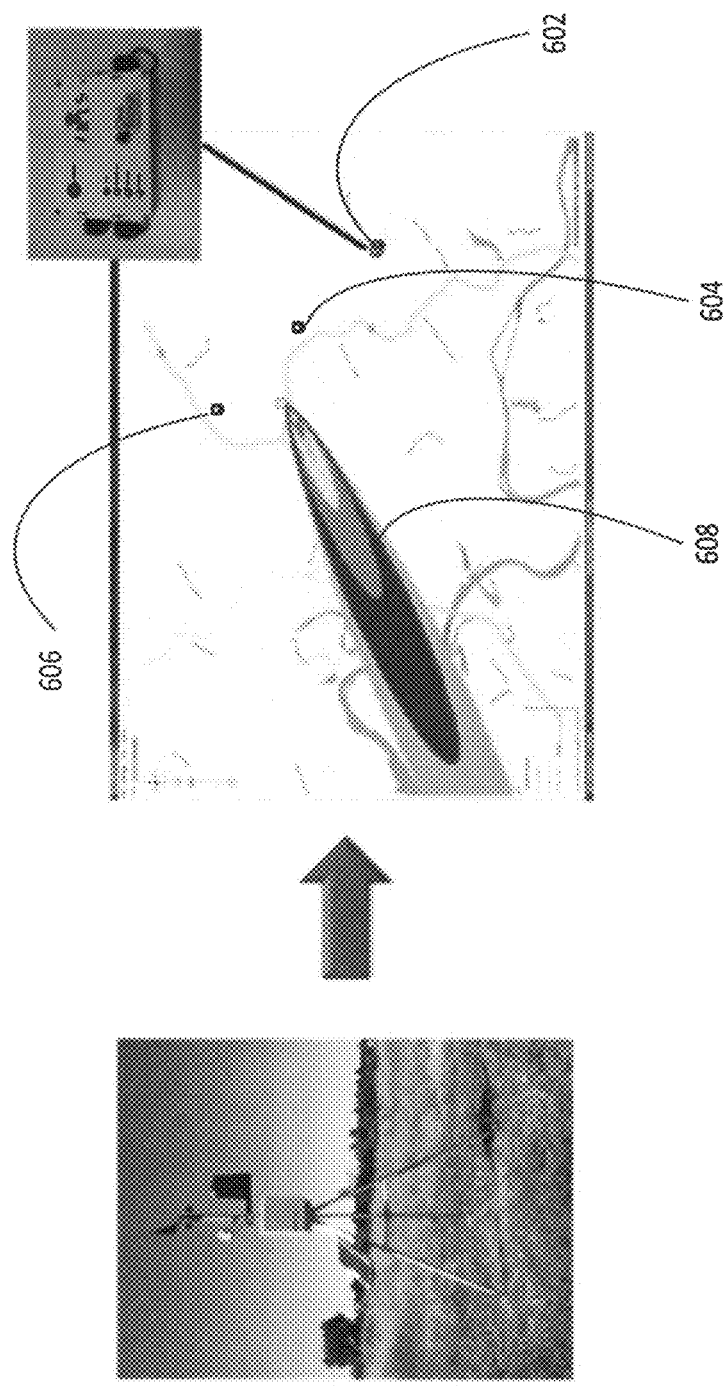
FIG. 6 shows an exemplary RSP sampling with active real-time weather data.

The system 100 models plumes and their dispersions 608 as shown in FIG. 6. Since dispersion refers to what happens to media after its introduction, understanding the weather patterns near it is processed to identify and possibly control the dispersion by enabling remediating actions. Meteorology stations 602-606 shown as the blue icons may wirelessly transmit such information including ground and air temperature, relative humidity, barometric pressure, precipitation, wind and speed direction, rain amounts/snow depth, for example, through the satellite router 102 and gateway 104 or directly through gateway 104 to the information repository and intelligent server 106. The Meteorology stations 602-606 may further transmit forecast data wirelessly through the gateway 104 to the information repository and intelligent server 106.

As shown in FIG. 6, a plume modeled by the information repository and intelligent server 106 may move away from its source and widens because of the entrainment of the surrounding media at or near its edges. The client-side image shown in FIG. 6 color codes the densities of the media from a point, line, area, or volume source. The red area represents a magnitude of concentration higher than the yellow area, which represents a magnitude of concentration higher than the green area, which represents a magnitude of concentration higher than dark blue area, which represents a magnitude of concentration higher than the light blue area. The concentration tracer level profiles accurately predict dispersion concentrations because it simulates dispersion events based on local meteorological information measured or forecasted by the meteorology stations 602-606 that are local to the source. The inclusion of the weather data makes dispersion model more useful and accurate than some models such as known Gaussian models because the model does not assume that the media it is predicting has a Gaussian distribution in changing weather conditions.

Figure 7:
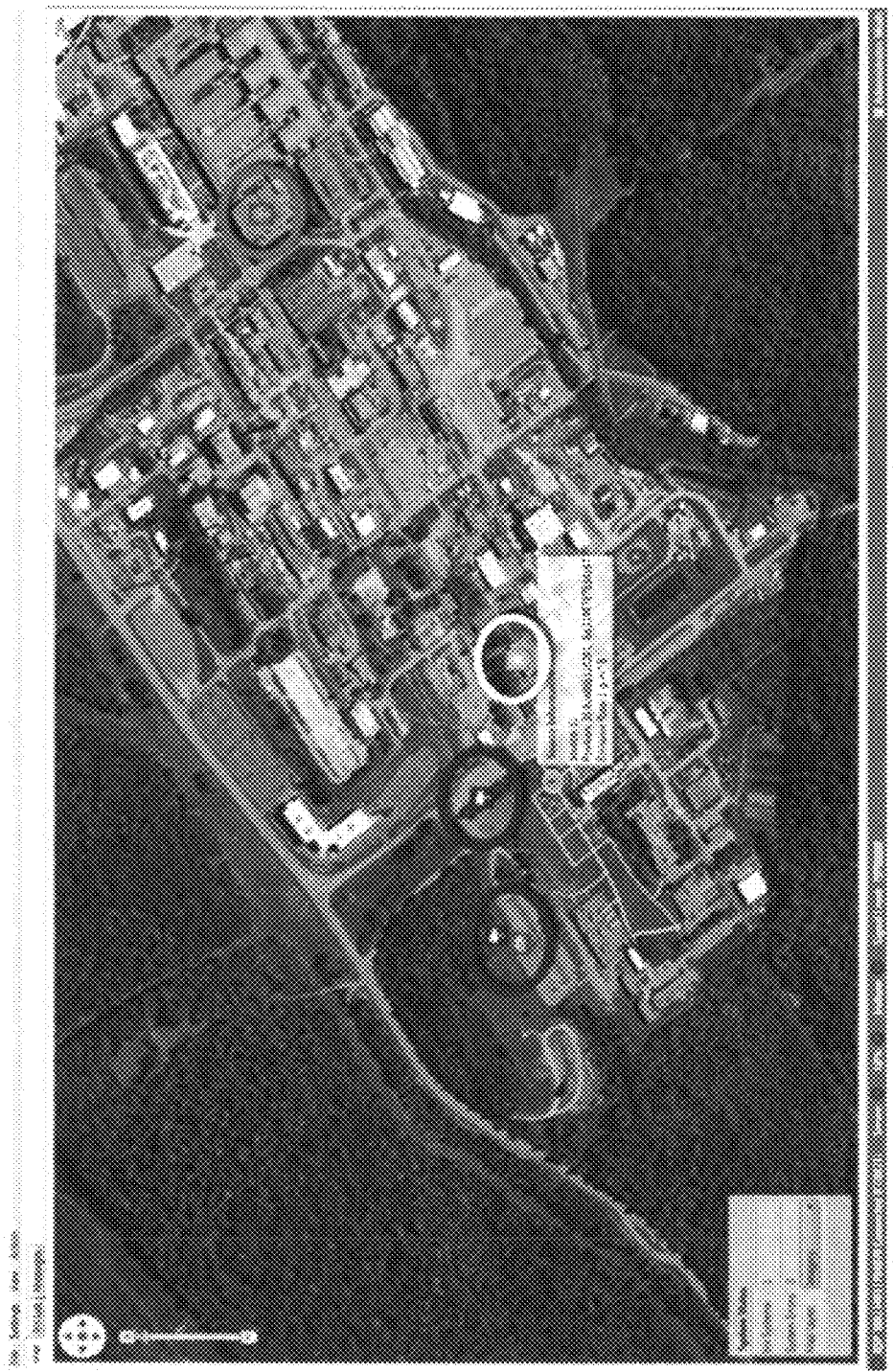
FIG. 7 shows an exemplary RSP (in red), weather stations (in blue), and a source location (in green).
Figure 8:
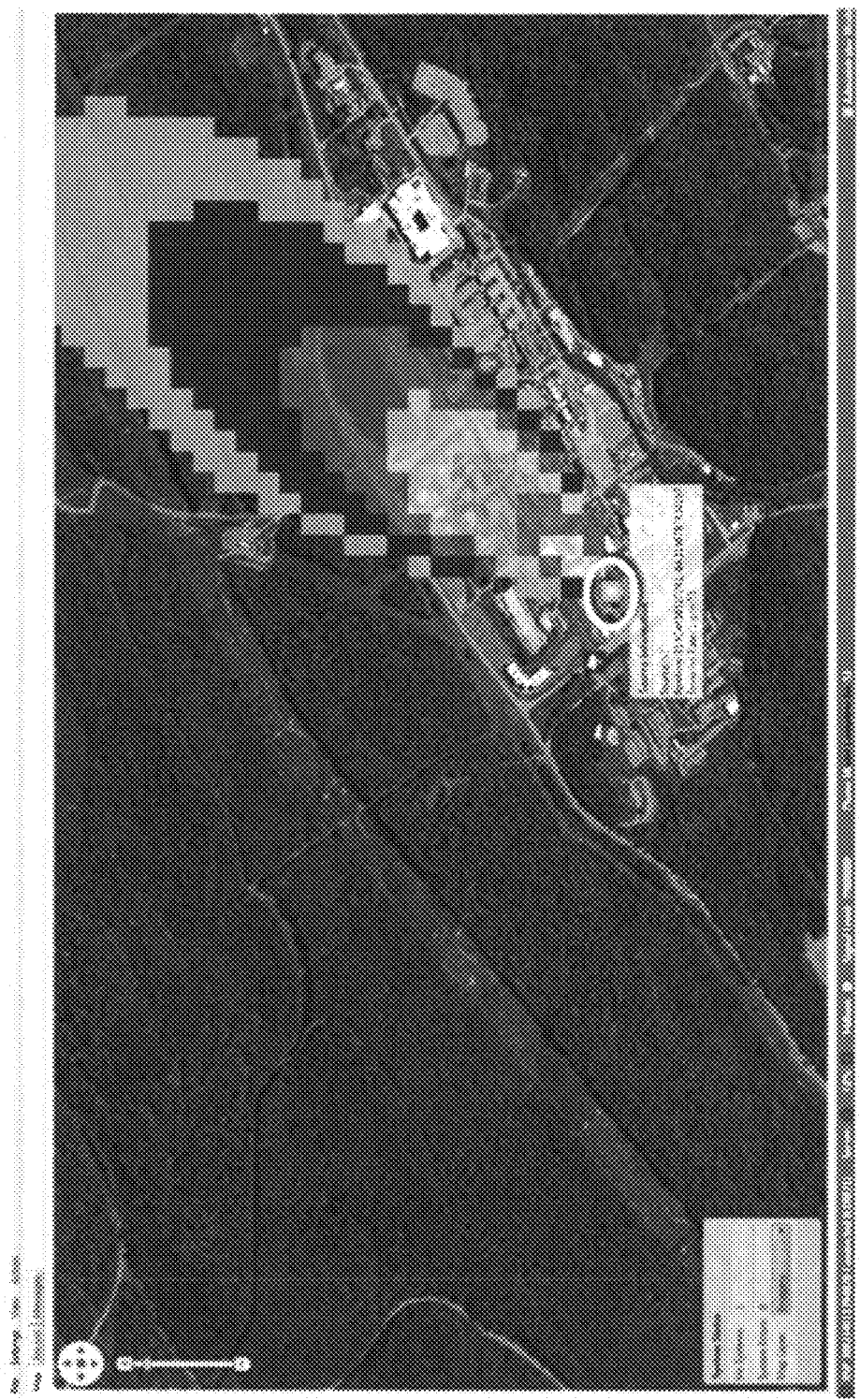
FIG. 8 is a graphic of a plume projected at the source location of FIG. 7.
Figure 9:
FIG. 9 shows the plume's dispersion of FIG. 8.

FIGS. 7 and 8 visually illustrate a three dimensional plume dispersion model positioned at an emission source (circled in white in FIG. 7) near weather stations (circled in blue in FIG. 7) and an off-line RSP (circled in red in FIG. 7) on a client-side image map. While the weather stations and RSP are shown as stationary platforms, the weather stations and RSP may also be part of one or more UAV's or its removable payload that may be dropped at a location that provides precise detection, measurements, and calculations close to the source. In FIG. 9, the projected dispersion path and concentration levels are shown in two dimensions with the concentration levels shown in red, pink, yellow, green, dark blue and light blue. Finer concentration resolutions such as those shown in high definition may be rendered in more colors in alternative systems.

Figure 10:
FIG. 10 shows a target monitoring area and an unmanned aerial vehicle (UAV).
Figure 13:
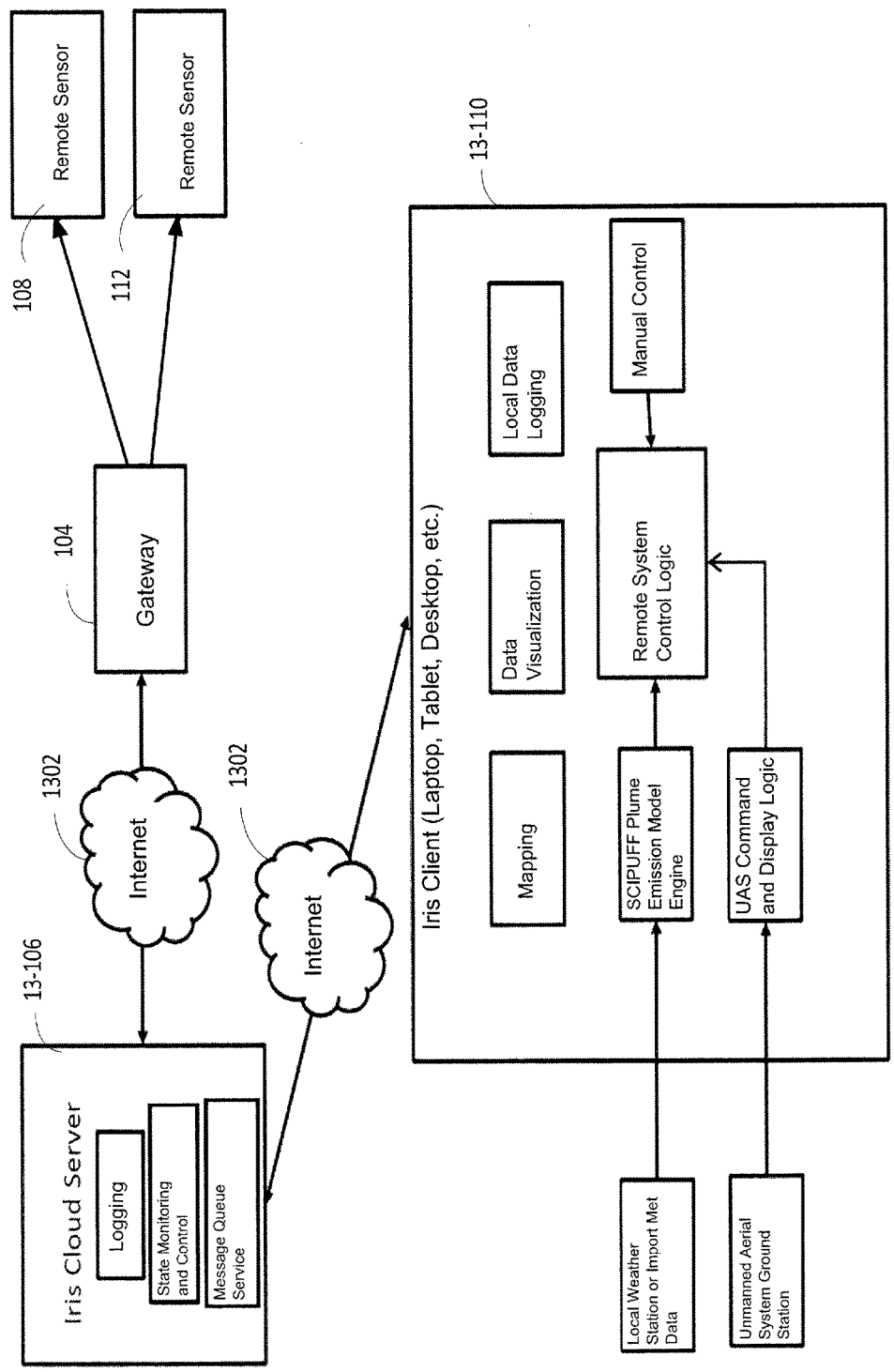
FIG. 13 is an alternate global plug-and-play automated configurable sensor control and data acquisition platform.
Figure 14:
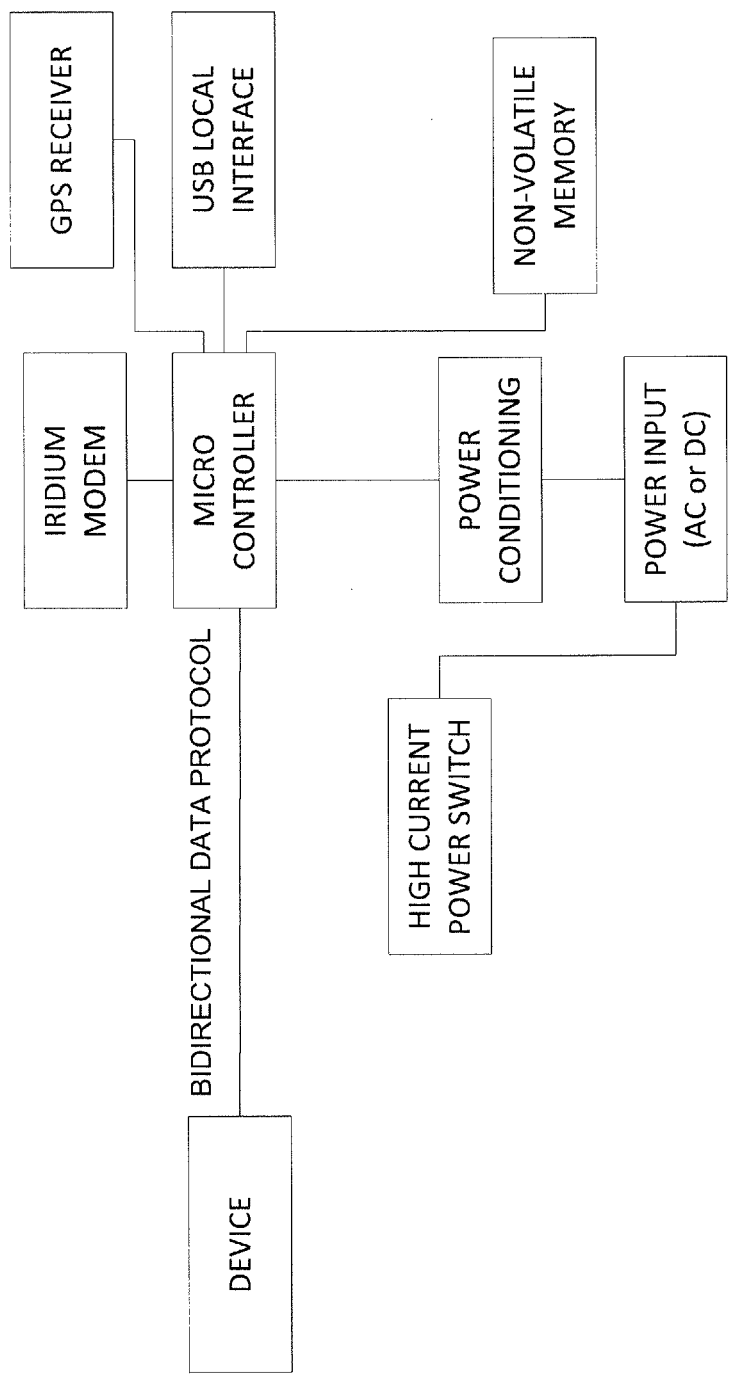
FIG. 14 is an exemplary RSP.
Figure 15:
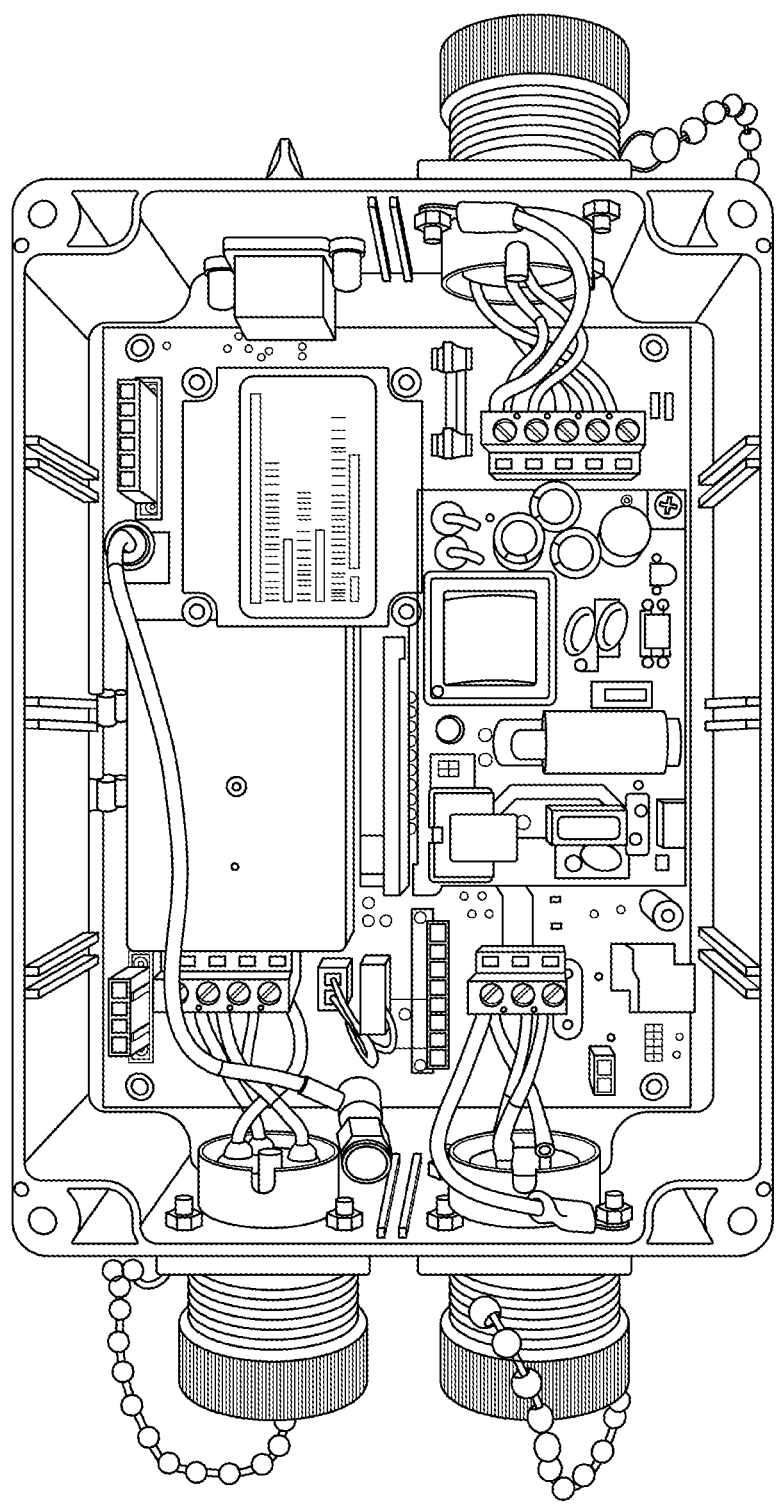
FIG. 15 is an exemplary RSP reduced to practice.

In FIG. 10 a wireless connection between the UAV 1002 the information repository and intelligent server 106 cedes control of the UAV 1002 from a user. In some systems short-range radar and/or lidar sensors embedded in the UAV's 1002 keep the UAV 1002 clear of obstacles and on track to the target 1004 by detecting approaching objects in some cases to the millimeter and keep the UAV 1002 at predetermined distance from the obstacles. The data is processed on-board the UAV 1002 or alternately by the information repository and intelligent server 106 through a wireless link that instructs the UAV 1002 to accelerate, bank, brake, turn, etc. As shown in FIG. 10, the UAV 1002 and the target 1004 may be tracked on a client-side image map that may allow user intervention to assume control or facilitate monitoring. When the target is a media dispersion, a spiral-shaped triple-colored galaxy plume may be rendered on the display representing the dispersion it is tracking. As the UAV 1002 approaches the target 1004 (as shown it is 113 meters away) the UAV 1002 transmits real time updates to the information repository and intelligent server 106 allowing it to track all levels of concentration from the highest concentrations of the plume at the highest to lowest levels of the plume that may vary depending on whether the emission is a buoyant plume, a dense plume, a passive plume, or a neutral plume. As the plume disperses over time UAV 1002 may track the dispersion rates, dispersion areas, and/or its respective concentrations. In some systems the UAV 1002 may drop or position an onboard payload, such as the payload of UAV 1002 shown in gray in response to a condition, event, or user command at one or multiple locations.

FIG. 11 is an exemplary remote monitoring process. The process detects media such as contaminants at 1102 through an RSP. The RSP is the interface between the remote sensor the satellite router that orbits the earth. Based on its configuration the RSP transmits data to information repository and intelligent server process that models the plume at 1104. Based on the plume model information repository and intelligent server process activates and configures mobile and static intelligent sensors that are a part of the RSP at 1008. In some alternative processes, the information repository and intelligent server process may create a virtual sensor through a virtual configuration file. The virtual sensor configuration file may define one or more of the input parameters the virtual sensor should meter or measure, the analytic to be performed, the output to be returned, and/or the port number where the output data is to be transmitted. Based on the virtual configuration file, an RSP may dynamically search, identify, and connect a sensor plug-in accessed locally through the RSP memory or remotely through a local wireless Internet Service Provider (ISP) or satellite router that may access a local area network library of sensor plug-ins. Once functional, the RSP and virtual sensor may stream the output to the information repository and intelligent server process.

If contaminates are shown or forecasted to spread through weather data and the plume models, the process enables, configures, and/or generates additional RSPs and/or sensors that can track and forecast the path and the flow rates of the gases and aerosols that may comprise the plumes in a predicted area. As the plume spreads or is projected to spread to an area the process activates and configures sensors at 1112 and 1108 in the projected contaminants paths (its geographic areas), harvests data from RSPs, and meteorological stations in or near its path automatically or through polling, and adjusts the plume model based on the newly harvested data to help identify the gases and aerosols (or other media), their respective concentrations, and the paths and rates that it will flow. The processes RSPs/sensors/virtual sensors and operations can match the real time characteristics of an event allowing the event to respond to one or more dispersions as it occurs (e.g., at least at the same rate data is received), creating, enabling, and/or positioning RSP's (e.g., through UAVs or mobile platforms) in projected paths, disabling RSP's or removing virtual plug-in sensors from RSPs that are no longer needed or are not within the projected plume path, while making corrections and enabling other sensors based on measurements, analytics, and forecasts.

While the communication between the RSPs and the satellite router and the ISP's may occur through packets through a packet switched protocol like a Transmission Control Protocol\Internet Protocol (TCP/IP) type Internet protocol, alternative communication protocols are used in alternate systems and processes. One alternate uses a modified linear network coding, which improves wireless bandwidth by an order of magnitude without adding base stations, routers, or spectrum. The modified linear network coding transforms the communication exchange by not resending packets that may be dropped or do not arrive at a destination. Instead of re-sending packets this alternate communication protocol transmits linear algebraic equations that describe the functional relationship between series of packets (two or more packets that are transmitted consecutively in some systems/processes and nonconsecutively in alternate systems/processes) so that when a packet does not arrive, the receiving device or process processes the algebraic equation to recreate the missing packet at the client-receiving device. Since the equation is an algebraic equation describing the relation between segments of packets, the load on the receiving client device is negligible. In an exemplary application coded packets are encoded using random linear network coding. The coded packets are encoded using an earlier sequenced packet and randomly generated coefficients, using a linear algebra function. The combined packet length is no longer than either of the two or more packets from which it is composed. When a packet is lost, the missing packet is mathematically derived from a later-sequenced packet that includes earlier-sequenced packets and the coefficients used to encode the packet. In yet another alternate communication system or process, the transmitting device may combine several packets into one same-sized packet using random linear coding. The same number of packets may be sent or received as would occur in normal TCP/IP type protocol. However, if a packet does not arrive at a destination the random linear coding in this alternate re-generates the original stream based on the packets interchangeability. The second alternative communication system significantly reduces the packets resent and the associated signaling needed to track the lost packets. Both exemplary protocols are stateless data transmissions that achieve higher speeds without link layer flow control slowing down the exchanges with retransmission requests. The systems/processes apply a mathematical approach to data error correction and data transmission redundancy.

FIG. 12 illustrates a second alternate global plug-and-play automated configurable sensor control and data acquisition platform. In this second alternate system the mapping software (that generates the client-side image maps), the data visualization software (that graphically/visually displays plume models and weather models), the plume modeling engine (that generates the plume models), the remote system control logic (that activates/configures and/or generates the sensors on the RSPs) and the processing of the weather data occur on the client device 12-110, while the state monitoring and control and logging software (that writes the log files) occurs on the information repository and intelligent server 12-106. FIG. 13 illustrates a third global plug-and-play automated configurable sensor control and data acquisition platform. In this third alternate system the hardware satellite router 102 of FIG. 1 is replaced with an ISP hardware interface to the Internet 1302, the hardware information repository and intelligent server 106 is moved to a cloud computing platform, and the RSP data is supplemented with local weather station data collected from a UAV or ground station, other ground station data, and UAV transmitted data at the alternate client device 13-110. FIG. 14 is an exemplary RSP deployment that may provide global control from a connected device. And, FIG. 15 is an exemplary RSP reduced to practice.

The methods, devices, systems, and logic described above may be implemented in many different ways in many different combinations of hardware, software or both hardware and software. For example, in some modes of operation the mapping and data visualization on the client side devices may generate the client-side image maps that identify when RSPs report a detection (e.g., a hit) in real time. The real time reporting and rendering on the client side maps may visualize one or more dispersions as they occur. In another mode of operation, the remote system control logic may actuate all of the RSPs in communication with the client device at once to detect and render visualizations of the dispersions as they occur. The methods, devices, systems, and logic described above may make use of many types of dispersion models as well as hybrids of one or more dispersion models including: Lagrangian models, Eulerian models, dense gas models, box models, Gaussian models, etc. The models may represent one or more buoyant plumes, dense gas plumes, passive and/or neutral plumes, etc.

All or parts of the system may comprise one or more controllers, one or more microprocessors (CPUs), one or more signal processors (SPU), one or more graphics processors (GPUs), one or more application specific integrated circuit (ASIC), one or more programmable media or any and all combinations of such hardware. All or part of the logic, specialized processes, and systems described may be implemented as instructions for execution by multi-core processors (e.g., CPUs, SPUs, and/or GPUs), controller, or other processing device including exascale computers and compute clusters, and may be displayed through a display driver in communication with a remote or local display, or stored in a tangible or non-transitory machine-readable or computer-readable medium such as flash memory, random access memory (RAM) or read only memory (ROM), erasable programmable read only memory (EPROM) or other machine-readable medium such as a compact disc read only memory (CDROM), or magnetic or optical disk. Thus, a product, such as a computer program product, may include a storage medium and computer readable instructions stored on the medium, which when executed in an endpoint, computer system, or other device, cause the device to perform operations according to any of the process descriptions or hardware descriptions above.

The systems may be implemented through processors (e.g., CPUs, SPUs, GPUs, etc.), memory, interconnect shared and/or distributed among multiple system components, such as among multiple processors and memories, including multiple distributed processing systems. Parameters, databases, software and data structures used to evaluate and analyze these systems or logic may be separately stored and managed, may be incorporated into a single memory or database, may be logically and/or physically organized in many different ways, and may be implemented in many ways, including data structures such as linked lists, programming libraries, or implicit storage mechanisms. Programs may be parts (e.g., subroutines) of a single program, separate programs, application program or programs distributed across several memories and processor cores and/or processing nodes, or implemented in many different ways, such as in a library, such as a shared library. The library may store virtual sensor configuration files that may generate micro sensor plug-ins as described herein. The virtual sensors may be generated dynamically, and in real-time which may include for example, configuring devices on the RSP's such as a spectrometer comprising a light source and camera that may be part of some RSP's or UAV's. The software makes use of the RSP's camera to image spectra of a source by capturing an images and comparing the underlining emission lines that are captured to a library of emission lines stored in a memory. By measuring the electromagnetic spectrum a source absorbs or emits, the virtual sensor can determine the molecular composition of the source/target. A virtual sensor may also enable accelerometers on the RSPs, for example, that can measure the rate of change of velocity and detect the orientation of the RSP or UAV, should the RSP or UAV change positions. The RSPs may also communicate with some or every active sensor and plug-in sensor and collect data from the external and internal sensors too. Once the RSP gathers all of the information, it generates a file that may be autonomously transmitted (e.g., an asynchronous transmission) or transmitted on demand. While various embodiments have been described, it will be apparent to those of ordinary skill in the art that many more embodiments and implementations are possible.

The term "coupled" disclosed in this description may encompass both direct and indirect coupling. Thus, first and second parts are said to be coupled together when they directly contact one another, as well as when the first part couples to an intermediate part which couples either directly or via one or more additional intermediate parts to the second part. The term "substantially" or "about" encompass a range that is largely (ninety five percent or more), but not necessarily wholly, that which is specified. It encompasses all but a significant amount. When devices are responsive to or occur in response to commands events, and/or requests, the actions and/or steps of the devices, such as the operations that devices are performing, necessarily occur as a direct or indirect result of the preceding commands, events, actions, and/or requests. In other words, the operations occur as a result of the preceding operations. A device that is responsive to another requires more than an action (i.e., the device's response to) merely follow another action.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

What is claimed is:

1. A global communication and control process comprising:
    detecting a dispersion of contaminants data through a plurality of distributed remote sensor platforms connected to one or more sensors on a remote device;

transmitting the detection data from the distributed remote sensor platforms to a radiation tolerant satellite router;

processing the detection data at a gateway that connects to the radiation tolerant satellite router, the gateway converts the detection data to a compatible protocol used by a hardware server, transferring the detection data to the hardware server;

generating a plume model in response to the detection data and a meteorological data that models dispersion plumes; and activating selected one or more sensors of the one or more sensors in response to a forecasted dispersion area generated from the plume model;

where a communication between the radiant tolerant satellite router and the gateway occurs through a packet switch protocol that transmits an algebraic equation that describes a functional relationship between a series of packets transmitted from the radiation tolerant satellite router to the gateway.

2. The process of claim 1 where the process deactivates the selected one or more sensors in response to the forecasted dispersion area generated from the plume model.

3. The process of claim 1 where the one or more sensors comprise static or mobile sensors and virtual sensors that are generated from a virtual configuration file that generate the virtual sensors and connect the static or mobile sensors to one or more of the plurality of distributed remote sensor platforms, where the virtual sensors determine molecular composites of materials.

4. The process of claim 1 where the one or more sensors are mobile sensors that are a unitary part of an unmanned aerial vehicle.

5. The process of claim 4 where the activation of the selected one or more sensors comprises configuring the one or more sensors in response to the generated plume model.

6. The process of claim 1 where the generation of the plume model occurs at least as fast as a same rate as the detection data is received at the gateway enabling the process to direct and control the selected one or more sensors in real time.

7. The process of claim 1, where the packet switched protocol does not send replacement packets when packets are lost.

8. The process of claim 7 where the packet switched protocol executes a modified linear network coding to generate the replacement packets for the lost packets.

9. The process of claim 8 where the series of packets is transmitted nonconsecutively.

10. The process of claim 7 where the packet switched protocol executes a random linear coding that combines several packets into a same sized packet.

11. The process of claim 1 further comprising regenerating the plume model in response to the detection data and meteorological data that models the dispersion plumes and the detection data received from the one or more sensors that were activated in response to the forecasted dispersion area generated from a prior plume model.

12. The process of claim 1 where the detection data samples an aerosol or sample of air.

13. The process of claim 1 where the one or more sensors comprises mobile sensors, buoyed sensors, and static sensors.

14. The process of claim 1 where at least some of the one or more sensors are integrated into a UAV.

15. A global communication and control process comprising:

detecting a dispersion of contaminants data through a plurality of distributed remote sensor platforms connected to one or more sensors on a remote device;

transmitting the detection data from the distributed remote sensor platforms to a radiation tolerant satellite router;

processing the detection data at a gateway that connects the radiation tolerant satellite router to the gateway that converts the detection data to a compatible protocol used by a hardware server and transferring the detection data to the hardware server;

generating a plume model in response to the detection data and a meteorological data that models dispersion plumes; and activating selected one or more sensors of the one or more sensors in response to a forecasted dispersion area generated from the plume model;

where the detecting, the transmitting, the processing, the generating, and the activating occur autonomously in real-time without human intervention; and where a communication between the radiant tolerant satellite router and the gateway occurs through a packet switch protocol that transmits an algebraic equation that describes a functional relationship between a series of packets that recreates packets missing from a transmission from the radiation tolerant satellite router.

16. An autonomous global communication and control system comprising:

a central processor processing executable code accessed from a random access memory, in which the executable code:

detects a dispersion of contaminants data through a plurality of distributed remote sensor platforms connected to one or more sensors on a remote device;

transmits the detection data from the distributed remote sensor platforms to a radiation tolerant satellite router;

processes the detection data at a gateway that connects the radiation tolerant satellite router to the gateway that converts the detection data to a compatible protocol used by a hardware server and transferring the detection data to the hardware server;

generates a plume model in response to the detection data and a meteorological data that models dispersion plumes; and activates selected one or more sensors of the one or more sensors in response to a forecasted dispersion area generated from the plume model;

where a communication between the radiant tolerant satellite router and the gateway occurs through a packet switch protocol that transmits an algebraic equation that describes a functional relationship between a series of packets that recreates packets missing from a transmission from the radiation tolerant satellite router.

* * * * *